(12) United States Patent
House et al.

(10) Patent No.: US 7,934,622 B2
(45) Date of Patent: May 3, 2011

(54) SYSTEM AND METHOD FOR DISPENSING DEHYDRATED CULTURE MEDIA POWDER

(75) Inventors: Arthur G. House, Chevy Chase, MD (US); Kevin P. Klink, Middletown, MD (US); William J. Richman, Frederick, MD (US)

(73) Assignee: Mediatek, LLC, Frederick, MD (US)

( * ) Notice: Subject to any disclaimer, the term of this patent is extended or adjusted under 35 U.S.C. 154(b) by 1060 days.

(21) Appl. No.: 11/417,091

(22) Filed: May 3, 2006

(65) Prior Publication Data

US 2007/0095854 A1 May 3, 2007

Related U.S. Application Data

(60) Provisional application No. 60/732,774, filed on Nov. 1, 2005.

(51) Int. Cl.
*B67D 1/00* (2006.01)
*C12M 1/16* (2006.01)
*C12N 1/00* (2006.01)
*B65D 25/08* (2006.01)
*C12M 3/00* (2006.01)

(52) U.S. Cl. .......... 222/63; 206/219; 206/221; 206/222; 206/268; 222/196; 222/412; 435/243; 435/253.6; 435/286.2; 435/289.1

(58) Field of Classification Search .......... 206/219, 206/221, 222, 268; 222/195, 412; 435/243, 435/253.6, 286.2, 289.1
See application file for complete search history.

(56) References Cited

U.S. PATENT DOCUMENTS

| | | | | |
|---|---|---|---|---|
| 3,077,254 A | * | 2/1963 | Goldfarb | 194/294 |
| 3,406,870 A | | 10/1968 | Arneson | |
| 3,501,379 A | | 3/1970 | Tate | |
| 3,810,535 A | * | 5/1974 | Phipps | 194/296 |
| 5,000,314 A | * | 3/1991 | Fuller et al. | 206/221 |
| 5,385,403 A | | 1/1995 | Knight et al. | |
| 5,899,248 A | | 5/1999 | Anderson | |
| 5,913,453 A | * | 6/1999 | Coleman et al. | 221/24 |
| 6,173,117 B1 | | 1/2001 | Clubb | |
| 6,199,605 B1 | | 3/2001 | Inaba et al. | |
| 6,530,499 B1 | * | 3/2003 | Coleman et al. | 221/24 |
| 2004/0026452 A1 | | 2/2004 | Santiago et al. | |
| 2004/0155069 A1 | | 8/2004 | Fontaine et al. | |
| 2006/0252146 A1 | | 11/2006 | House et al. | |

FOREIGN PATENT DOCUMENTS

GB 2187373 A 9/2009

OTHER PUBLICATIONS

Gumball Machine, (http//: www.Gumballs.com, Printed May 7, 2008 and Feb. 1, 2009).*
Sharpe et al.1972, Machine for Automatic Bacteriological Pour Plate Preparation, Applied Microbiology, vol. 24, No. 1, Jul. 1972, pp. 70-76.*
Serpent & Dove advertisement, "New: Magnetic Mount for Vibrating Motors," www.serpent-dove.com, May 13, 2005.
Kinematics Models 4400/VC and 4400/TX, www.kinematics.com/products/fillingMachines.html, 2005.
Cremore, 2004; http://www.cremora.com/faqs.html Printed Feb. 21, 2009.

* cited by examiner

*Primary Examiner* — Jon P Weber
*Assistant Examiner* — Kailash C Srivastava
(74) *Attorney, Agent, or Firm* — Global IP Counselors, LLP

(57) ABSTRACT

An improved system and method for dispensing dehydrated culture media (DCM) powder into containers for preparation as a culture media. The manual and automated systems and methods operate to dispense DCM powder, as well as liquid, into vessels or media preparation instruments in a manner to avoid DCM dust inhalation by persons in the surrounding area and contamination of equipment and surfaces in the surrounding area. The system can further comprise a carousel arrangement that permits dispensing of DCM powder from multiple containers at multiple volumes and rates. In addition, the containers have a particular configuration for use with the system and method, such as the carousel arrangement, to avoid errors, promote repeatability and eliminate dusting. The containers can also include a device, such as an auger, to facilitated measured dispensing of the DCM powder automatically or manually into a flask, automated media sterilizers or other instruments.

15 Claims, 14 Drawing Sheets

SYSTEM AND METHOD FOR DISPENSING DEHYDRATED CULTURE MEDIA POWDER

This application claims benefit from provisional Application No. 60/732,774 filed on Nov. 1, 2005, the entire content being incorporated herein by reference.

CROSS-REFERENCE TO RELATED APPLICATIONS

Related subject matter is disclosed in U.S. application Ser. No. 11/119,912, filed May 3, 2005, and in U.S. application Ser. No. 11/119,792, filed on May 3, 2005, the entire content of each being incorporated herein by reference.

BACKGROUND OF THE INVENTION

1. Field of the Invention

The present invention provides an improved system and method for dispensing dehydrated culture media (DCM) powder into containers for preparation of culture media. More particularly, the present invention relates to improved manual and automated systems and methods for dispensing DCM powder into vessels or media preparation instruments in a sanitary manner to avoid contamination by DCM powder dust to the surrounding area.

2. Description of the Related Art

Microbiology laboratories are required to produce large quantities of agar based growth media to use in the growth of bacteria and other microorganisms. Regardless of the specific agar media formulation used, most media are prepared by mixing powdered dehydrated culture media (DCM) with water and then sterilizing the mixture in an autoclave to insure the growth media is free of contamination. The dehydrated media powder, which is ground very fine, is typically delivered to the laboratory in plastic containers of varying sizes. A laboratory technician will typically scoop or pour out and weigh the required amount of DCM powder, add the appropriate amount of water, and mix and warm the mixture using, for example, a magnetic stirring motor with stir bar. Once the DCM and water have been completely mixed, the mixture is sterilized by autoclave or media preparator.

As used in most laboratories, DCM is a very light and fine powder. Some DCM formulations are highly toxic and all are irritants to some degree. When poured, DCM often forms a cloud of dust that rises above and around the technician who is dispensing the powder. This "media cloud" or "dusting" causes several problems. Often the technician will inhale DCM dust, which can be a health hazard. Additionally, as the dust settles it leaves a film of agar on surrounding laboratory surfaces. Because DCM typically is used in areas that tend to be warm and moist due to the close proximity of steam-producing autoclaves, the media dust leaves a sticky film that is difficult to clean and that increases the likelihood of surface contamination. Moreover, because the DCM is a fine powder, it tends to penetrate into very small spaces in the laboratory, including the inside surfaces of scientific instruments where the resulting film can cause damage and excess wear over time.

Another problem is that the process of dispensing DCM is time consuming since a precise quantity should first be weighed prior to adding water. A further problem is that mixing large batches of DCM with water, e.g., batches of certain types of media larger than 10 liters, often requires DCM and water to be added alternately in limited quantities each time to avoid clumping of the media. This increases the time needed to create the media, contributes to inaccuracies and errors and increases the likelihood of DCM dusting. A further problem is that technicians sometimes are imprecise in their measurements of DCM or water. It is also important for technicians to be able to readily identify different containers including different types of media cultures without close inspection, to thus increase the efficiency of the dispensing process.

Accordingly, a need exists for an improved system and method for dispensing DCM in a sanitary manner to avoid contamination to surrounding areas and minimize exposure to technicians and other personnel.

SUMMARY OF THE INVENTION

An embodiment of the present invention provides an automated or manual system for delivering DCM powder to a preparation instrument or a container in a sanitary manner to prevent media dusting by eliminating or substantially reducing the formation of the DCM media cloud during the preparation process. An embodiment of the present invention further provides a method for a convenient, rapid, exact and reproducible dispensing of DCM into either flasks or automated media sterilizers or other instruments.

The embodiments of the present invention further are capable of dispensing an appropriate amount of water or liquid into a media sterilizer or other instrument or container while simultaneously dispensing DCM powder in the proper amount and in a manner so as to avoid clumping. The metering device can be programmable to dispense the appropriate admixture of water and DCM depending on the concentration desired. The embodiments of the present invention are also able to prevent or minimize laboratory errors by applying color coding or other identification indicia to the DCM containers to indicate specific media formulations, thereby reducing the likelihood that the incorrect DCM formulation will be used by a technician.

The embodiments of the present invention further provide a system comprising a carousel arrangement that permits dispensing of DCM powder from multiple containers at multiple volumes and rates. The embodiments of the present invention also provide a DCM container that is equipped with a device, such as an auger, that can facilitate measured dispensing of DCM powder automatically or manually into a flask, automated media sterilizers or other instruments.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENTS

Figure 1:
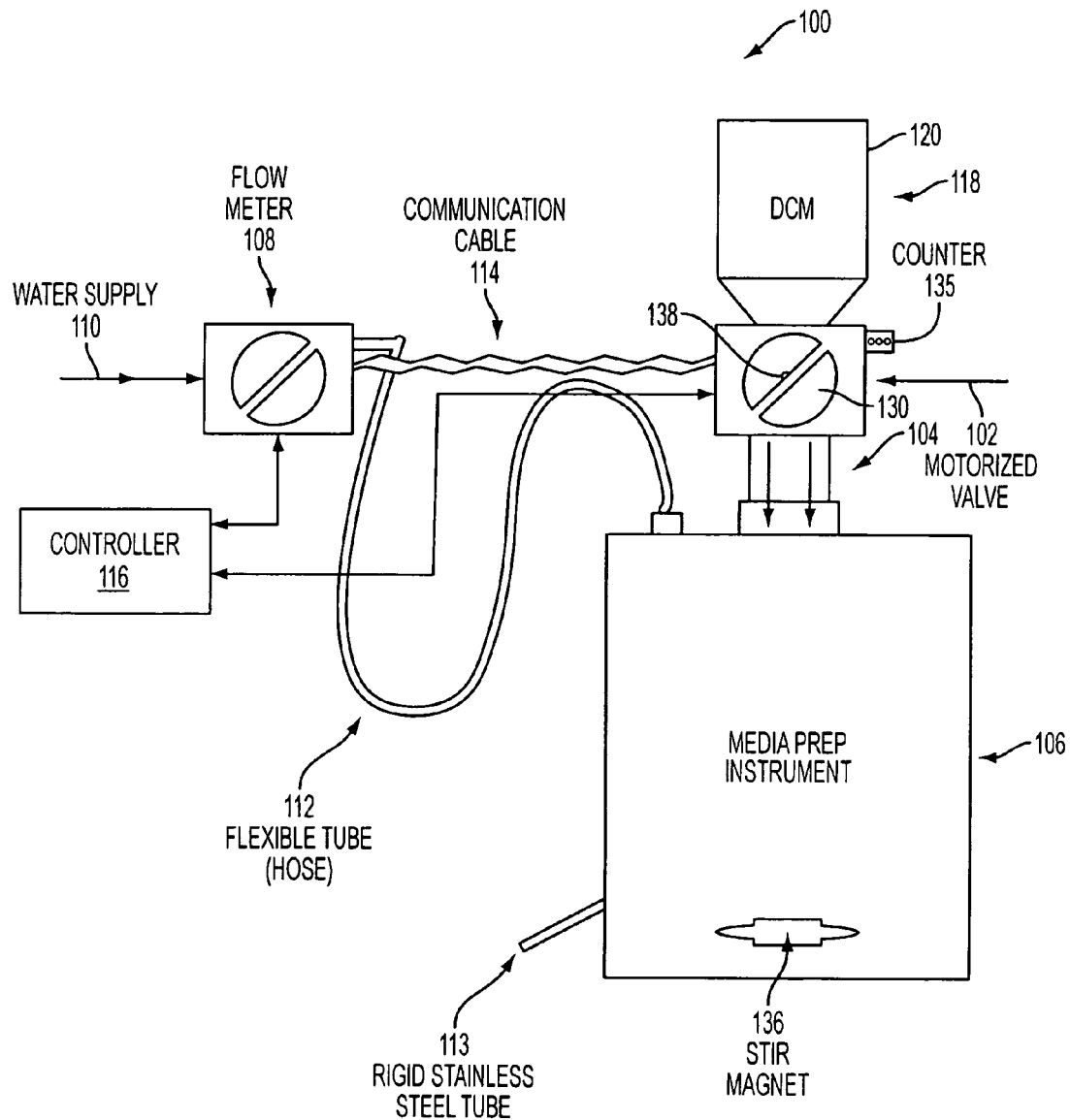
FIG. 1 is a conceptual block diagram illustrating an example of an automated system for dispensing DCM powder into a media preparation instrument according to an embodiment of the present invention.

FIG. 1 illustrates an automated system 100 for dispensing DCM powder according to an embodiment of the present invention. As illustrated, the automated system 100 includes a motorized valve assembly 102 that is connected via a conduit 104 to a media preparation instrument 106. The media preparation instrument can be any type of instrument such as the MediaPrep line from Systec Gmbh, Wettenberg, Germany, Masterclave line from AES Laboratoire, Rennes, France, or MediaClave line from Integra Biosciences, Chur, Switzerland, each of which are commercially available.

As further illustrated, the system further includes a flow meter 108. The flow meter is electronically controlled with a digital or analog input and output for communication with a secondary device used to inject the DCM powder into the system. The flow meter can work on the basis of peristaltic action or other common commercial methodologies such as magnetic, ultrasonic, positive displacement or differential pressure. The flow meter instrument can be any type of instrument such as the AES PM05 from AES Laoratoire, Rennes, France, or the Perimatic GP or Perimatic Premier from Jencons Scientific, Inc., Bridgeville, Pa., that is connected to a water supply 110 or other liquid supply and provides water or other liquid to the media preparation instrument 106 in a regulated manner via flexible tube 112 as discussed in more detail below. The tube 112 is connected to a rigid tube 113 made of, for example, stainless steel or any other suitable material, and which extends near the bottom of the interior of the media preparation instrument 106 to minimize clumping of the DCM powder 120 and to improve mixing. The rigid tube 113 allows water to be added below the surface line of the DCM mixture to prevent or decrease the incidence of splashing or bubbling to prevent or substantially prevent, or at least minimize, the contact of water with the media entry port. A flexible tube may be utilized in place of the rigid tube 113; provided such flexible tube is configured so as to prevent or decrease the incidence of splashing or bubbling in the media preparation device. In practice, the tube 113 can be of any suitable material, such as rigid plastic, flexible plastic, bendable metal, a flexible hose, and so on, as long as it is positioned to prevent or substantially prevent the incidence of splashing or bubbling and its opening is at a sufficient distance from the media entry port. The motorized valve assembly 102 and flow meter 108 are connected by a communication cable 114 so that the rate at which the DCM powder is dispensed by the motorized valve 102 is coordinated with the rate at which liquid is dispensed into the media preparation instrument 106 by the flow meter 108 under the control of a controller 116, which can be a processor or any type of computer as can be appreciated by one skilled in the art. The controller 116 can be programmable by the technician or other suitable personnel as desired and with ease to control the desired dispensing rate of the DCM powder and liquid as discussed in more detail below. As further illustrated, the motorized valve 102 receives a container 118 in which the DCM powder is stored.

Figure 2:
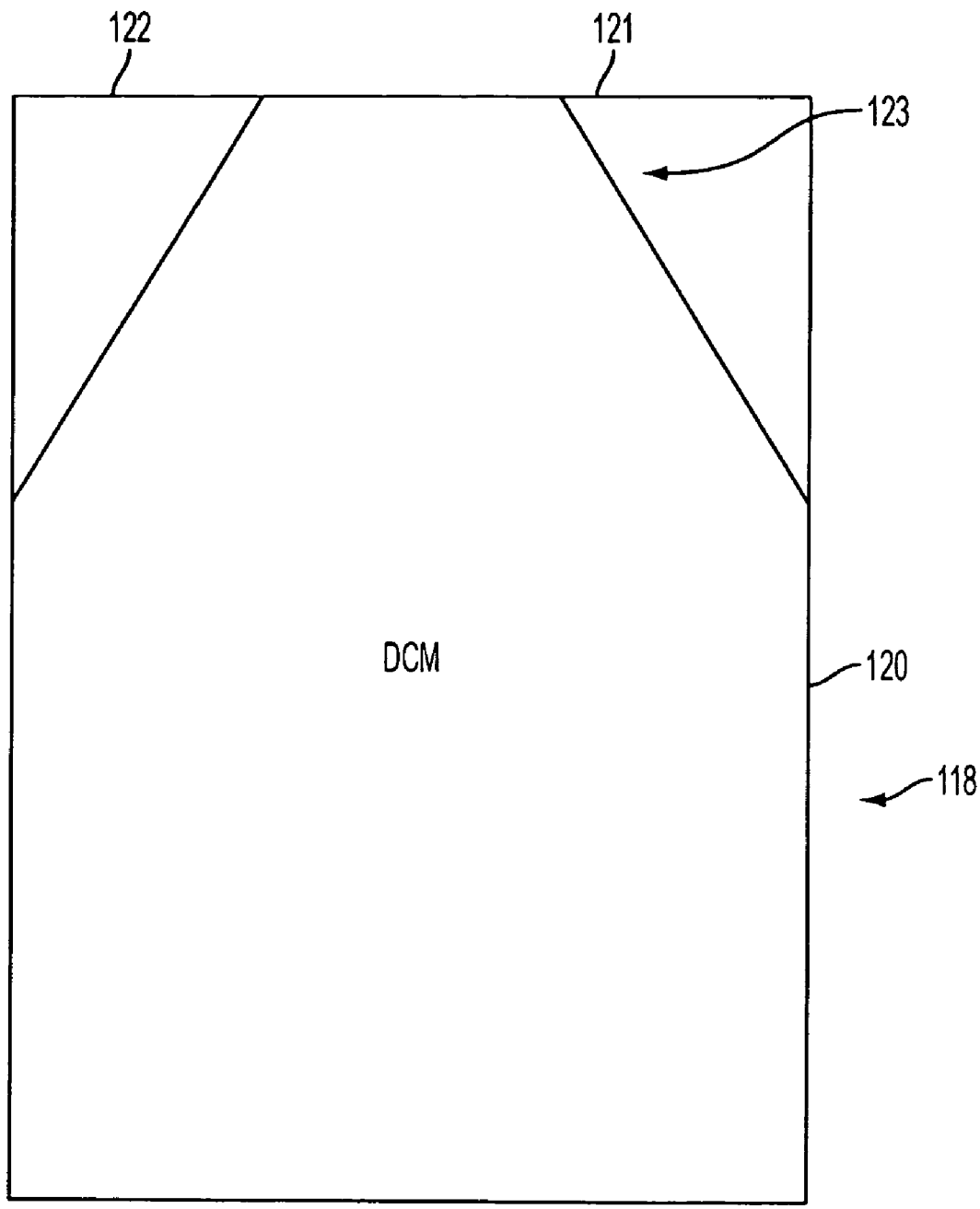
FIG. 2 is an example of a container which stores the DCM powder according to an embodiment of the present invention.
Figure 3:
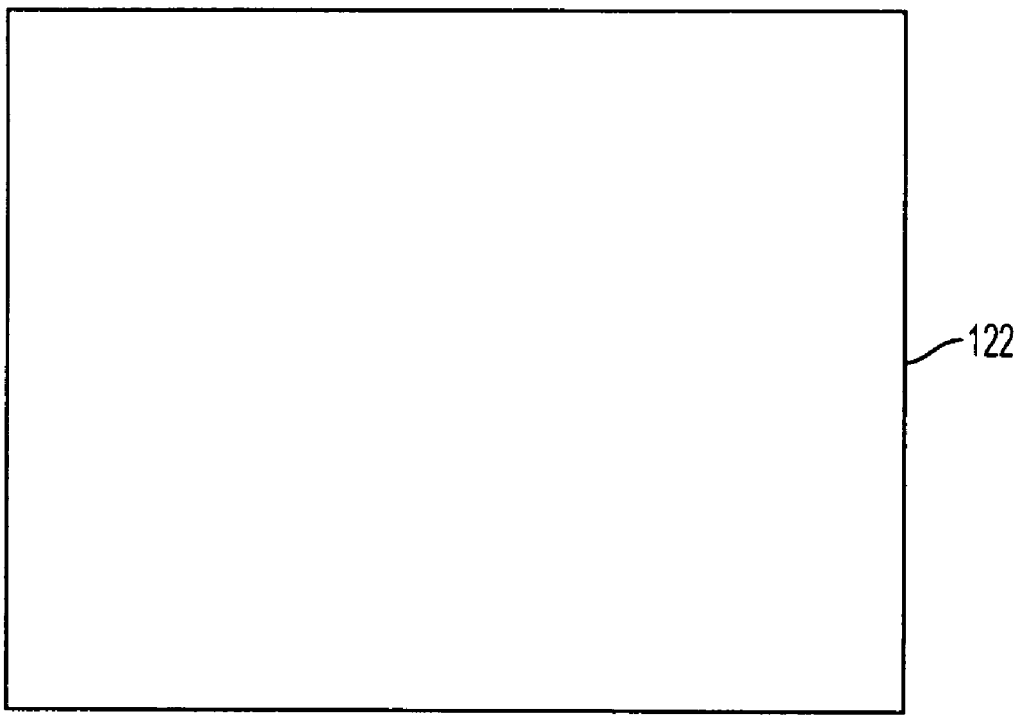
FIG. 3 is a top view of the container as shown in FIG. 2.

An example of a container for storing the DCM powder is shown in FIG. 2. In particular, the container 118 includes a container portion 120 and a cap 122. The container portion 120 can be any shape, although according to an embodiment of the present invention, it is advantageous for stacking purposes for the container to be shaped in the form of a rectangle or square having flat or substantially flat sides as shown in FIG. 2 and in the top view of FIG. 3. As further illustrated in FIG. 3, the cap 122 is preferably square shaped and has a flat or substantially flat top surface to allow the containers to be stacked vertically. The width and length of the cap 122 can correspond to the width and length of the container portion 120 as shown, or can be less than or greater than the width and length of the container portion 120, as deemed suitable for storage and stacking purposes.

In addition, for identification purposes, the container portion 120 and the cap 122 can be coded with a color or other indicator representing the contents of the container 118. For instance, this identification can be a color coding (e.g., red, green, blue, etc.) that is present on portions or the entirety of the container portion 120 and cap 122, a type of indicia (e.g., numbers, letters or alphanumeric symbols) on the container portion 120 and cap 122 representing the content of the container, and/or a bar code representing the content of the container 118. Various safety warnings and other relevant information can also be present on the container portion 120, cap 122 or both. Also, the container portion 120 and cap 122 can be made of any suitable material, such as plastic or various polymers, and can be opaque, or can be translucent so that a technician can readily determine the amount of DCM powder remaining in the container. Furthermore, the mouth of the container portion 120 is tapered or conical in shape so as to allow the DCM powder to readily flow from the container portion 120 when the container portion 120 is set in an upside down position with the cap 122 removed, and includes threads 121 as indicated. The mouth of the container portion 120 and the cap 122 can have threads 123 so that the cap 122 can be screwed onto exterior threads on the container portion 120. The container portion 120 can also be configured to include threads 121 on its interior wall near its opening. In this event, the container portion 120 can be screwed onto the motorized valve assembly 102 of FIG. 1 or the valve assembly 146 of FIG. 6, or directly onto the inlet of the media preparation instrument 106, regardless of whether the motorized valve assembly 102, valve assembly 146 or the inlet of the media preparation instrument 106, has interior or exterior threads. Alternatively, the cap 122 can be snap-fit onto the container portion 120, and the container portion 120 can simply be placed in an inverted manner so that its opening is received into the opening in the motorized valve assembly 102, valve assembly 146 or the inlet of the media preparation instrument 106.

Figure 4:
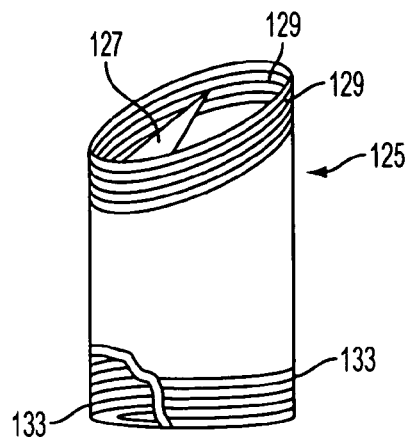
FIG. 4 illustrates an example of an adapter according to an embodiment of the present invention, that can be used with the container shown in FIG. 2.

In addition, it should be noted that the container portion 120 can have a volume that contains a pre-measured, pre-packaged quantity of DCM powder for a single-use, so that the container 118 can be discarded after its DCM powder contents has been dispensed as discussed in more detail below. It should be further noted that the container 118 can alternatively be configured as a burstable pouch or bag, for example, that contains a pre-measured, pre-packaged amount that can be dispensed directly into the media preparation instrument 106, into the media preparation instrument 106 via an adapter 125 as shown in FIG. 4, or into the motorized valve assembly 102 when pressure is applied to the container portion 120 to burst the container 120, and then the container portion 120 can be discarded. Concerning the adapter 125, as indicated in FIG. 4, the adapter 125 can be shaped at an angle, or can include a lancet 127, such that when the container portion 120 is mated with the adapter 125, the lancet 127 or angled portion of the adapter 125 pierces a membrane (e.g., a rupturable membrane) present at the mouth of the container portion 120. Furthermore, the adapter can have threads 129 that mate with the threads 123 on the outside of the container portion 120 so that the container portion 120 can be screwed onto the adapter 125. It is further noted that the threads 123 can also be present on the outside of the adapter 125 as indicated, to mate with interior threads of the container portion 120 should such an arrangement be necessary. The other end of the adapter 125 can include threads 133 that can be on the exterior surface of the adapter 125, the interior surface of the adapter 125 (as indicated by the breakaway section), or both, to allow the adapter 125 to mate with the motorized valve assembly 102, valve assembly 146 or the inlet of the media preparation instrument 106, regardless of whether the threads of the valves 102 or 146, or at the inlet of the media preparation instrument 106, are exterior or interior.

Figure 5:
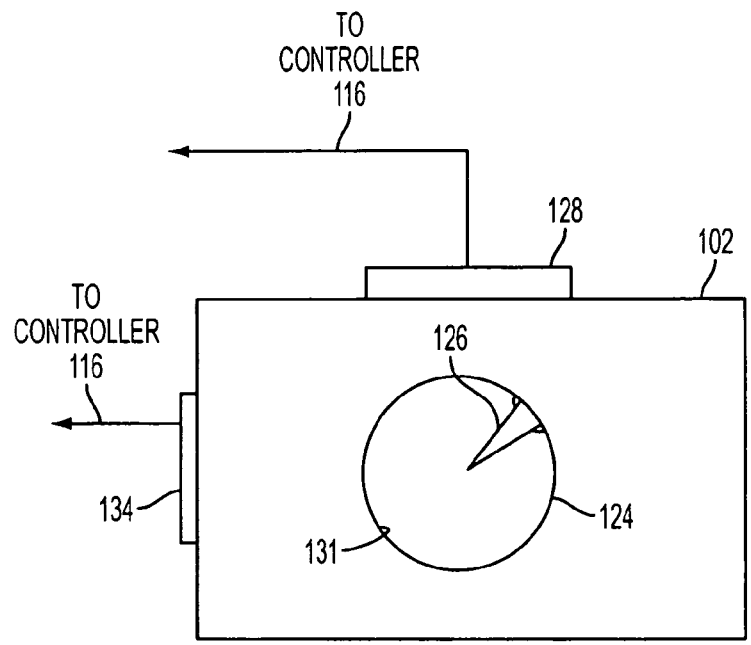
FIG. 5 is a detailed top view of the portion of the motorized valve assembly of the system shown in FIG. 1 that receives the mouth of the DCM container according to the embodiment of the present invention.

An example of the operation of the automated system 100 will now be described with reference to FIG. 1. As indicated, the cap 122 is removed from the container 118 and the container portion 120 is placed in an upside-down vertical or substantially vertical position on the top of the motorized valve assembly 102. As shown in FIG. 5, the mouth 124 of the motorized valve assembly 102 can have a lancet 126 or other suitable puncturing mechanism for puncturing any membrane (e.g., a rupturable membrane) that may be present at the mouth of the container portion 120, so that the DCM powder can be gravity-fed into the motorized valve assembly 102. The inner surface of the mouth 124 of the motorized valve assembly 102 can also include threads 131 that can mate with the threads 123 at the outside mouth of the container portion 120 as the container portion 120 is mated with the motorized valve assembly 102. Alternatively, the mouth of the container portion 120 can simply mate with the mouth 124 of the motorized valve assembly 102 in any suitable manner. As noted above, the adapter 125 can be used to couple the container portion 120 to the mouth 124 of the motorized valve assembly 102. In this regard, the adapter can have threads 133 that mate with the threads 131 on the inner surface of the mouth 124 of the motorized valve assembly 102. In any event, the mating of the container portion 120 and the mouth 124 of the motorized valve assembly 102, either directly or via the adapter 125, as well as the mating of the container portion 120 with the media preparation instrument 106 directly or via the adapter 125, form a closed or substantially closed system that eliminates or at least substantially eliminates DCM dust formation outside of the media preparation instrument 106. The mouth 124 of the motorized valve assembly 102 can alternatively be configured to mate with a container 118 that is configured as a burstable pouch or bag as discussed above, either directly or via the adapter 125 in any of the manners described above, so that when pressure is applied to the container portion 120, the pre-measured amount of DCM powder is dispensed into the motorized valve assembly 102 while maintaining the closed system to eliminate or at least substantially eliminate DCM dusting, and then the container portion 120 and cap 122 can be discarded.

Figure 6:
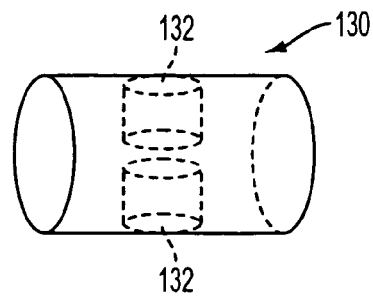
FIG. 6 illustrates an example of the features of the rotatable valve of the valve assembly shown in FIG. 1 for dispensing the DCM powder in a measured fashion according to an embodiment of the present invention.

As further illustrated in FIG. 5, the motorized valve assembly 102 can include a motor 128, such as a DC servo motor, a stepper motor, or any other suitable motor, that can be controlled by the controller 116 to rotate a rotatable valve 130 of the motorized valve assembly 102 that is shown in FIG. 1 and in more detail in FIG. 6. As indicated, the rotatable valve 130 includes wells 132 having a volume corresponding to a desired volume or mass of DCM powder (e.g., 15 grams) that is to be dispensed into the media preparation instrument 106. That is, the rotatable valve 130 is rotated at a desired rate as controlled by the controller 116 to periodically dispense the appropriate amount of DCM powder into the media preparation instrument 106 via the conduit 104. In addition, as the rotatable valve 130 is being rotated under the control of the controller 116, the flow meter 108 is controlled by the controller 116 to dispense an appropriate amount of liquid into the medium preparation assembly 106 via the tube 112. The ratio of dehydrated media to liquid is user controllable. For example, in a 100 liter preparation, one-fifth of the total DCM to be solubilized is added with every 20 liters of water. The user is able to define any ratio of total DCM to water, e.g., ¼ DCM combined incrementally with ¼ water or ⅓ DCM combined incrementally with ⅓ water. Accordingly, the rotatable valve 130 can be rotated more rapidly to dispense the DCM powder into the media preparation instrument 106 at a faster rate, while the controller 116 can proportionately control the flow meter 108 to increase the flow of liquid into the media preparation instrument 106. The motorized valve assembly 102 can further include a counter 135, such as a mechanical or digital counter as known in the art, that counts the number of rotations of the rotatable valve 130, and can be automatically or manually reset to zero after the desired amount of DCM powder has been dispensed.

It should be also noted that the rotatable valve 130 can be removed and replaced with another rotatable valve having wells of a different volume which thus feed a greater amount or lesser amount of DCM powder into the media preparation instrument 106 per each rotation. Furthermore, as shown in FIG. 5, the motorized valve assembly 102 can include an agitator 134, such as a vibrating coil or any other suitable component, to shake or vibrate the motorized valve assembly 102 to allow the DCM powder to more freely flow through the motorized valve assembly 102 and conduit 104 into the media preparation instrument 106.

It should also be noted that the rotatable valve 130 can include a handle 138 that can be turned manually if is desired to operate the rotatable valve 130 manually. The flow meter 108 can also be operated manually if desired. As further indicated, the media preparation instrument 106 includes a stirrer magnet 136 as known in the art which can provide further stirring and agitation of the powder and liquid mixture in the media preparation instrument 106. It can be further noted that the controller 116 can be connected by any suitable means to the controller (not shown) of the media preparation instrument 106 to increase or decrease the rate of stirring by the stirring magnet 138 depending on the rate of deposit of DCM powder and liquid by the motorized valve assembly 102 and flow meter 108. Accordingly, this system 100 allows for the accurate dispensing of DCM powder and liquid into the media preparation instrument 106 in a clean and sanitary manner, with little or no waste of the DCM powder, minimal contamination of the surrounding areas due to dusting, and minimal exposure to the lab technician and other personnel due to dusting.

Figure 7:
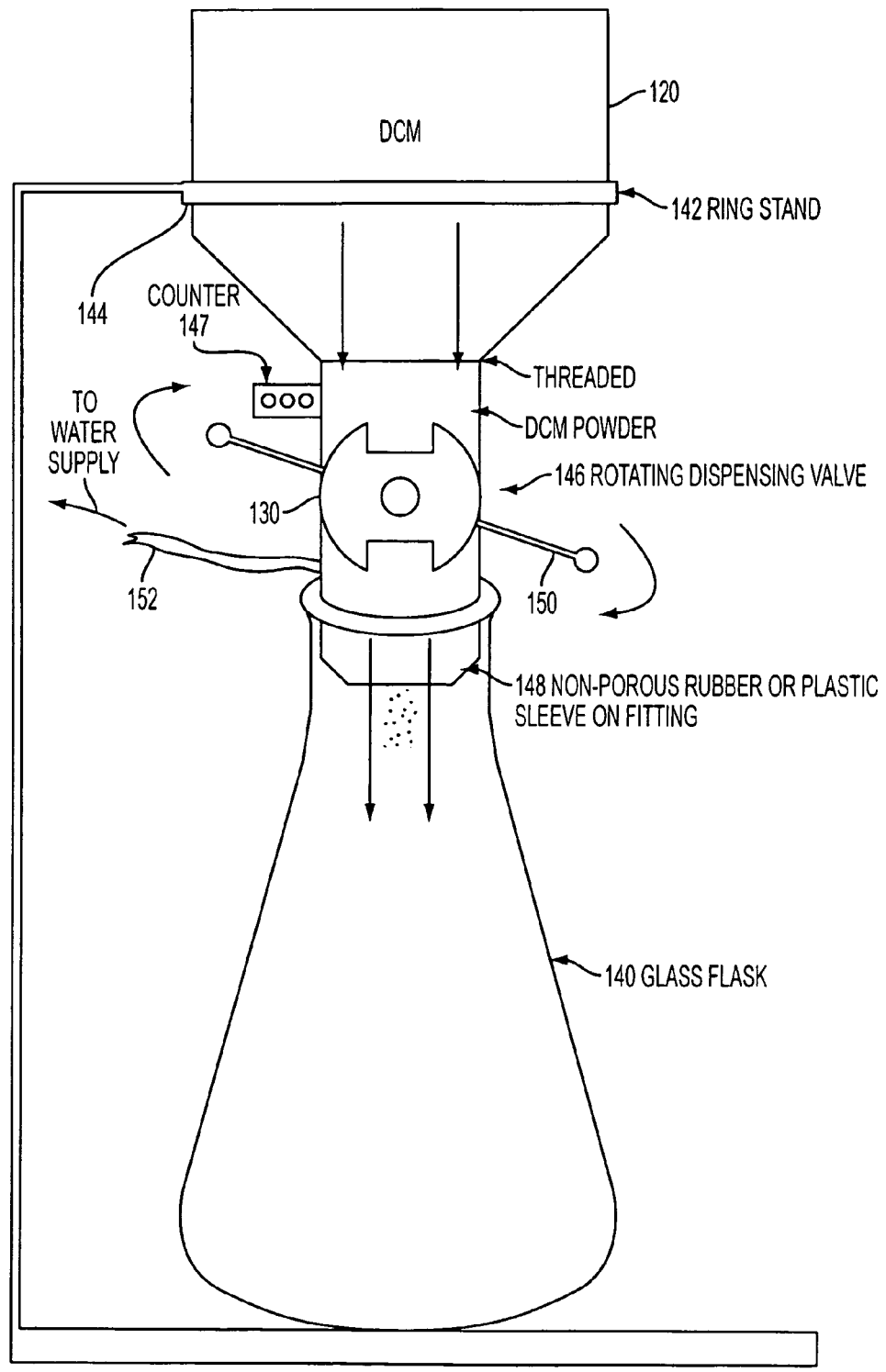
FIG. 7 illustrates an example of another system for dispensing DCM powder into a flask in a measured manner according to another embodiment of the present invention.

Although FIG. 1 and its related figures illustrate an automated system 100 for dispensing DCM powder into a media preparation instrument 106, the automated system 100, or a manual system, can be used to dispense the powder into another vessel or flask 140, such as an Erlenmeyer flask, as illustrated in FIG. 7. As indicated in FIG. 7, the system includes a ring stand 142 having a support 144 for supporting the container portion 120 in an upside down vertical or substantially vertical manner so that the DCM powder can flow by gravity into the valve assembly 146. The valve assembly 146 can include threads that mate with threads 123 on the outside of the mouth of the container portion 120, or the container portion 120 can simply be received into an opening in the valve assembly 146. Alternatively, the container portion 120 can be mated with the valve assembly 146 via the adapter 125 in the manner discussed above with regard to the motorized valve assembly 102, so as to form a closed or substantially closed system. Accordingly, the mating of the container portion 120 and the valve assembly 146, either directly or via the adapter 125, form a closed or substantially closed system that eliminates or at least substantially eliminates DCM dust formation outside of the vessel 140. The valve assembly 146 can alternatively be configured to mate, either directly or via the adapter 125, with a container 118 that is configured as a burstable pouch or bag as discussed above, so that when pressure is applied to the container 118, the pre-measured amount of DCM powder is dispensed into the valve assembly 146 when pressure is applied to the container 118 while maintaining the closed or substantially closed system to eliminate or at least substantially eliminate DCM dusting, and then the container 118 can be discarded. Furthermore, as can be appreciated from the above, the vessel 140 can be configured to mate with any of the types of container portion 120 directly or via the adapter 125 without using the valve assembly 146, and can have threads that mate with the threads 129 on the adapter 125 to facilitate the mating.

Also, the mouth of the valve assembly 146 can include a lancet similar to lancet 126 (see FIG. 5) to puncture any sealable membrane covering the mouth of the container portion 120. The valve assembly 146 further can be configured similar to the automated valve assembly 102, or can be configured solely as a manual valve assembly in which a user such as lab technician rotates the rotatable valve 130 of the valve assembly 146 by turning a knob 150 or by any other suitable mechanism. As with the motorized valve assembly 102, the rotatable valve 130 of the valve assembly 146 can be removed and replaced with a rotatable valve having different size wells to dispense a different amount of DCM powder into the flask 142 per each rotation. The valve assembly 146 can further include a counter 147, such as a mechanical or digital counter as known in the art, that counts the number of rotations of the rotatable valve 130, and can be automatically or manually reset to zero after the desired amount of DCM powder has been dispensed.

As further shown, the valve assembly 146 can include a non-porous rubber or plastic sleeve 148 to allow for mating with the mouth of the flask 142. Furthermore, the valve assembly 146 or the sleeve 148 can include an inlet tube 152 to allow water or other liquid to be manually or automatically fed into the flask 142 as the rotatable valve 148 is being manually or automatically rotated. The valve assembly 146 and the system in general can be automatically or manually agitated to allow the DCM powder to more freely fall into the valve assembly 146, and thus more freely into the flask 142. Accordingly, the system shown in FIG. 7 also provides an efficient and sanitary system for dispensing DCM powder into a container while avoiding waste and contamination of the surrounding area due to dusting and exposure to DCM powder inhalation due to dusting.

As shown in FIGS. 8-12, the system for dispensing DCM powder according to another embodiment of the present invention can be configured as a laboratory benchtop system 300. As with the embodiments discussed above, the system 300 allows for the predictable, accurate and reproducible preparation of culture media from DCM and has as a principal benefit the avoidance of DCM dust formation associated with culture media preparation otherwise encountered in laboratory practice.

The system 300 comprises a carousel stand 302 and a rotatable carousel 304. The carousel stand 302 and the rotatable carousel 304 can be made of plastic, metal, composite or any suitable material. The rotatable carousel 304 is coupled to the carousel stand 302 by a coupler 306 that couples to a pivot point 308 of the carousel stand 302 and can include any suitable rotating mechanism that enables the rotatable carousel 304 to rotate about 360 degrees with respect to the pivot point 308. The rotatable carousel 304 can be rotated manually, or the system 300 can further include a motor 310 that can automatically rotate the rotatable carousel 304 as desired under control of, for example, a computer (not shown).

Furthermore, the coupler 306 can have a chamber therein that is in communication with a main air hose 312 and a plurality of secondary air hoses 314 as shown. The main air hose 312 connects to a compressed air source (not shown), and the number of secondary air hoses 314 can, for example, correspond to the number of openings 316 in the rotatable carousel 304 that are each adapted to receive a DCM container 318 as discussed in more detail below. The coupler 306 therefore distributes the compressed air from the main air hose 312 to the secondary air hoses 314.

Figure 8:
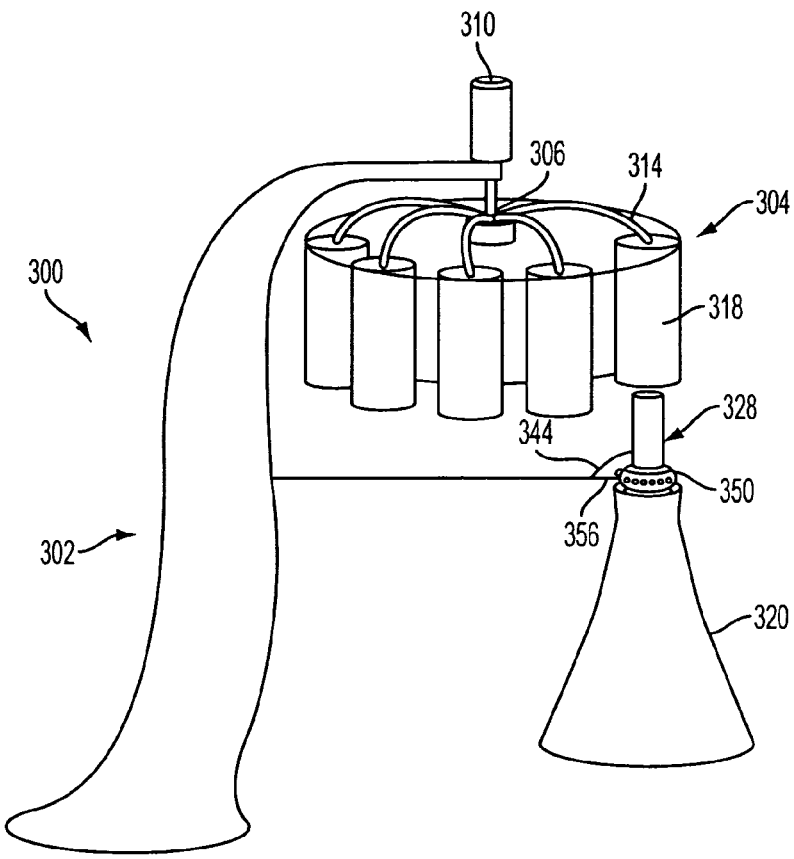
FIG. 8 is a perspective view illustrating an example of a carousel system for dispensing DCM powder according to an embodiment of the present invention.
Figure 9:
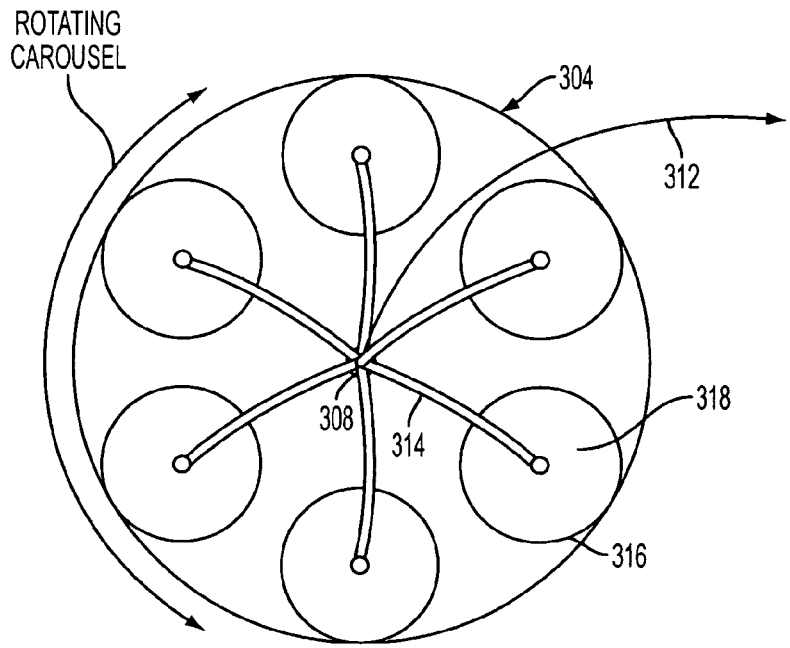
FIG. 9 is a top view of the carousel system shown in FIG. 8.

Specifically, as shown in FIG. 8, the rotatable carousel 304 is capable of holding one or more disposable containers 318 of various types of dehydrated culture media (DCM), that allows a user to select the type of DCM desired for use by rotating the desired container into position over the flask 320 into which the DCM will be deposited. The disposable containers 318 can be similar to the container portion 120 as discussed above, and can be round or, more particularly, hexagonally shaped so as to be suitable for stacking on their sides. The surfaces of the rotatable carousel 304 defining the openings 316 can each include mating grooves (not shown) that can mate with grooves on the exterior of a disposable container 318. Alternatively, the openings 316 can be shaped similarly to the outer shape of the disposable containers 318 (e.g., hexagonal) so that the disposable containers can be snap fit into the openings 316. The different disposable containers 318 can include different types of DCM powder or, for that matter, different types of materials altogether. The disposable containers 318 may be color coded to simplify the identification of the type of DCM power or other material to be used and to avoid mistakes by laboratory personnel.

Figure 10:
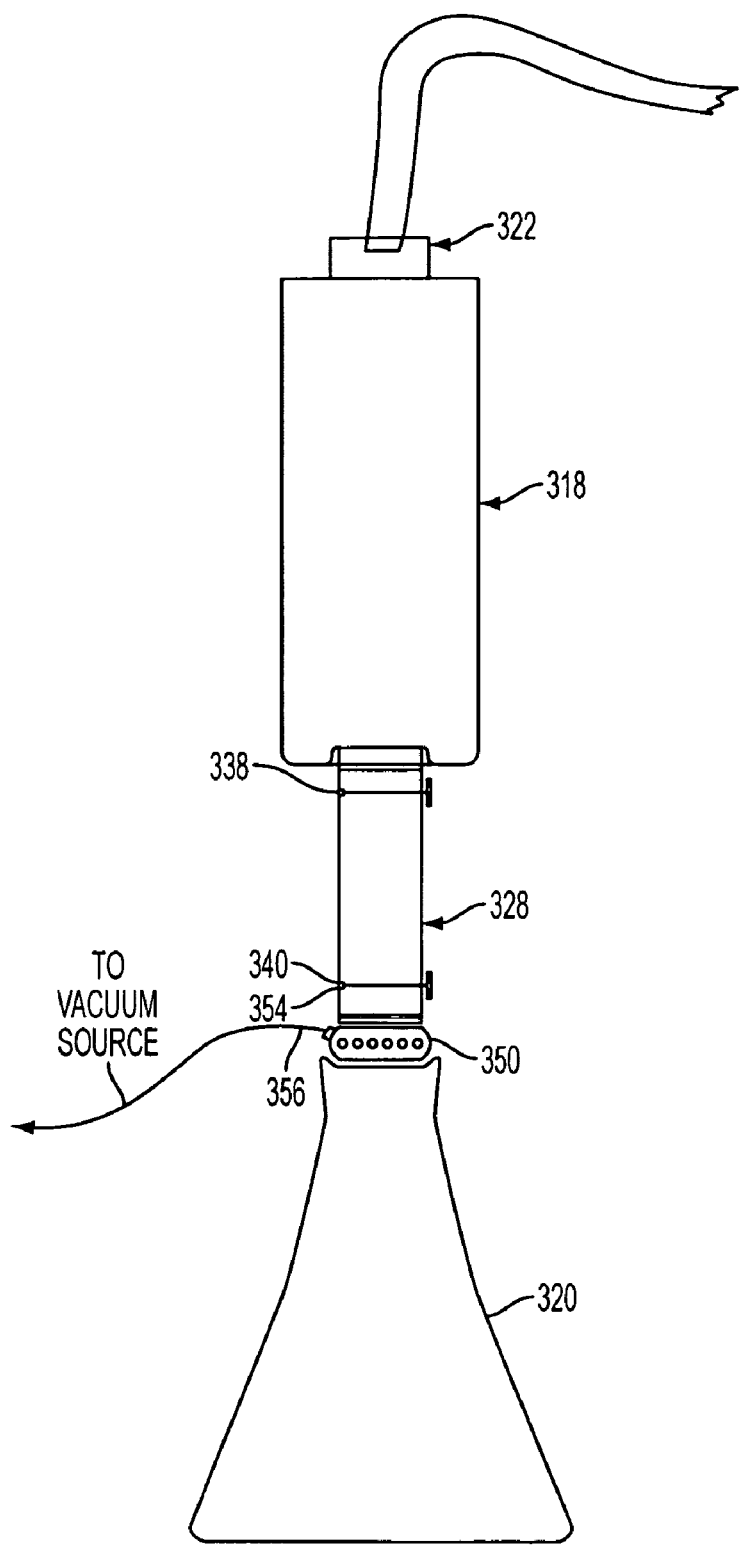
FIG. 10 is a detailed view of an example of a relationship between a DCM powder container, dispensing cylinder, flask and related components of the carousel system shown in FIG. 8.

As shown in more detail in FIG. 10, each of the secondary air hoses 314 can mate with the top of a respective disposable container 318 so that compressed air can be fed into the disposable container 318 to force out the DCM powder. Specifically, each secondary air hose 314 can include a connector 322 that can snap fit, screw into or otherwise mate with an opening 324 in the disposable container 318. The connector 322 alternatively can include a lance (not shown) that can pierce into the top of the disposable container 318 and thereby secure the secondary air hose 314 to the disposable container 318. Alternatively, the connector 322 can be present at the top of the disposable container 318 and can be configured to receive an end of the secondary air hose 314 to thus couple the secondary air hose 314 to the disposable container 318. As can be appreciated by one skilled the art, regardless of the manner in which the connector 322 is configured, the connector 322 can include a one-way valve (not shown) that permits air from the secondary air hose 314 to enter the disposable container 318 but does not permit the contents of the disposable container 318 to exit the disposable container if, for example, a negative pressure is inadvertently applied to the secondary air hose 314. The valve can be operated automatically or manually.

Figure 11:
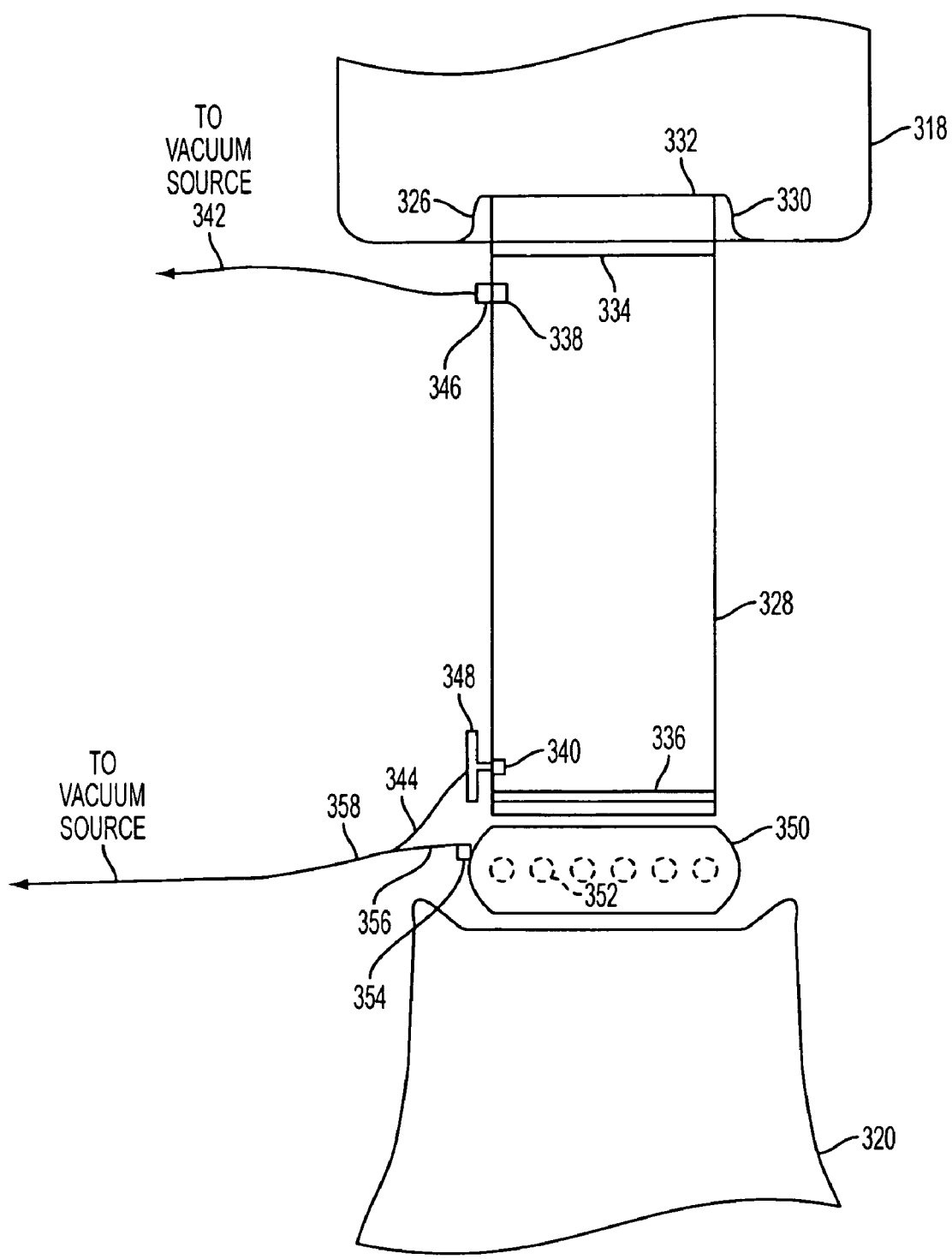
FIG. 11 is a more detailed view of an example of a relationship between a DCM powder container, dispensing cylinder, flask and related components of the carousel system shown in FIG. 8.
Figure 12A:
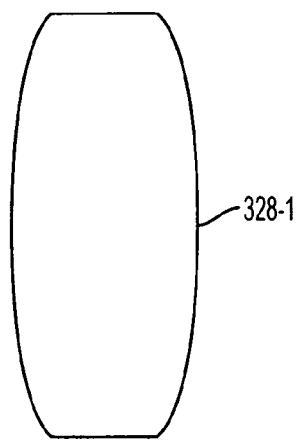
FIGS. 12A-12C are side views illustrating examples of different shapes of the dispensing cylinder used in the carousel arrangement shown in FIG. 8.
Figure 12B:
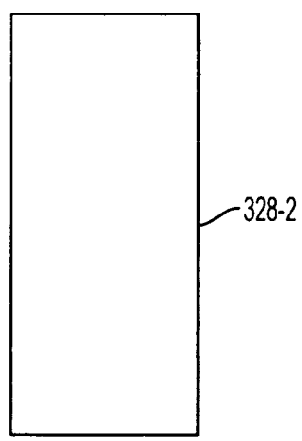
Figure 12C:
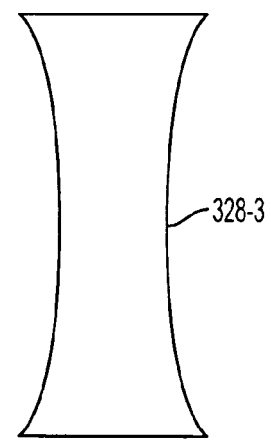

As further shown in FIG. 10 and a shown in more detail in FIG. 11, the bottom of the disposable container 318 can include an opening 326 that can mate with a tube 328 either by screwing, snap fitting or in any other suitable manner. Specifically, the surface of the disposable container 318 defining the opening 326 can include threads 330 that mate with threads 332 on the tube 328. Alternatively, one end of the tube 328 can include a lance (not shown) that can pierce into the disposable container 318 and thus secure the tube 328 to the disposable container 318.

The tube 328 further includes valves 334 and 336 positioned proximate to each end as illustrated. These values 334 and 336 can be membrane-type valves, or any suitable type of one-way valves that allow the contents of the disposable container 318 to enter and pass through the tube 328 in one direction (i.e., downward in FIG. 10). The valves 334 and 336 can be operated automatically or manually.

Is should be noted that the tube 328 has dimensions to accommodate a desired volume of DCM powder. For example, the cylindrically shaped tube 328 can have dimensions to accommodate 15 grams of DCM powder. The tube 328 can be configured differently to accommodate different volumes of DCM powder as discussed in more detail below.

As further shown in FIGS. 10 and 11, the tube 328 can include two side valves 338 and 340 that can allow air to pass through the value out of the tube 328 when the valves 338 and 340 are coupled to hoses 342 and 344 that are further coupled to a vacuum source (not shown). These valves 338 and 340 can further be coupled to filters 346 and 348 which couple to the hoses 342 and 344 and prevent DCM powder from exiting the tube 328 while allowing air to flow from the tube 328 into the hoses 342 and 344 when the vacuum is applied as discussed in more detail below.

FIGS. 10 and 11 also illustrate that a vacuum ring 350 can be coupled to one end of the tube 328 between the mouth of the flask 320 and the end of the tube 328. The vacuum ring 350 includes an opening 352 that permits DCM powder to pass from the tube 328 through the vacuum ring 350 and into the flask 320. The vacuum ring 350 further includes a plurality of interior openings 354 that communicate with the opening 352, and a hollow tap 354 to which a hose 356 can be connected. The hollow tap 354 communicates with the interior openings 354. The hose 356 can be connected to the vacuum source either in conjunction with hose 344 via a Y-connection 358, or independently.

When positive air pressure is applied to the top of the disposable container 318 via the secondary air hose 314, and a negative pressure is applied to the bottom of the container via tube 328 when a vacuum is applied to the hoses 342, 344 and 356, the DCM power is drawn from the disposable container 318, through the tube 328, and into the flask 320 in a measured manner. The amount of air pressure and vacuum pressure can be adjusted accordingly to adjust the rate of flow of the DCM powder into the flask 320. The vacuum ring 350 evacuates any DCM powder dust that may rise up from the mouth of the flask 320 when the DCM powder is flowing into the flask 320, thus eliminating or substantially eliminating the dusting problem as described in the Background section above.

It should also be noted that the DCM powder can be emptied into the flask 320 in a very precise and measured manner. For example, using gravity, agitation, vibration and/or mixing, as well as the appropriate amount of positive air pressure applied to the contents of the DCM container via secondary air hose 314, and the appropriate amount of vacuum pressure applied via hoses 342, 344 and 356, the DCM can be drawn into the tube 328 while the valve 336 at the bottom of the tube 328 remains closed. Once the tube 328 is filled, the valve 336 can be automatically or manually opened to allow the appropriate amount of DCM powder to be dispensed into the flask 320. At this time, a positive air pressure can be applied to the cylinder 328 via hoses 342 and 344 to assist in expelling the DCM powder from the cylinder 328. It should be noted that in this arrangement, it is advantageous for the vacuum ring 350 to be independently coupled to the vacuum source via hose 356 so that a vacuum can be applied to the vacuum ring 350 to suction away any DCM dust that may develop while the air pressure is being applied via hoses 342 and 344.

It is also desirable to use cylinder 328 of different volumes to allow for a differing rate of dispensing of the DCM powder. However, as can be further appreciated by the configuration of the system 300, it is important that the distance from the bottom of the vacuum ring 350 to the top of the mouth of the flask 320 be as small as possible without impeding the ability of the rotatable carousel 304 to rotate due to, for example, contact between the flask 320 and the vacuum ring 350. Therefore, it is important that the heights of the different volume cylinders 328 to be the same or substantially the same. Accordingly, as shown in more detail in FIGS. 12A-12C, the cylinder 328 can have different shapes such as cylinders 328-1, 328-2 and 328-3, so that these different cylinders 328 through 328-3 can have different volumes while having the same height.

Figure 13:
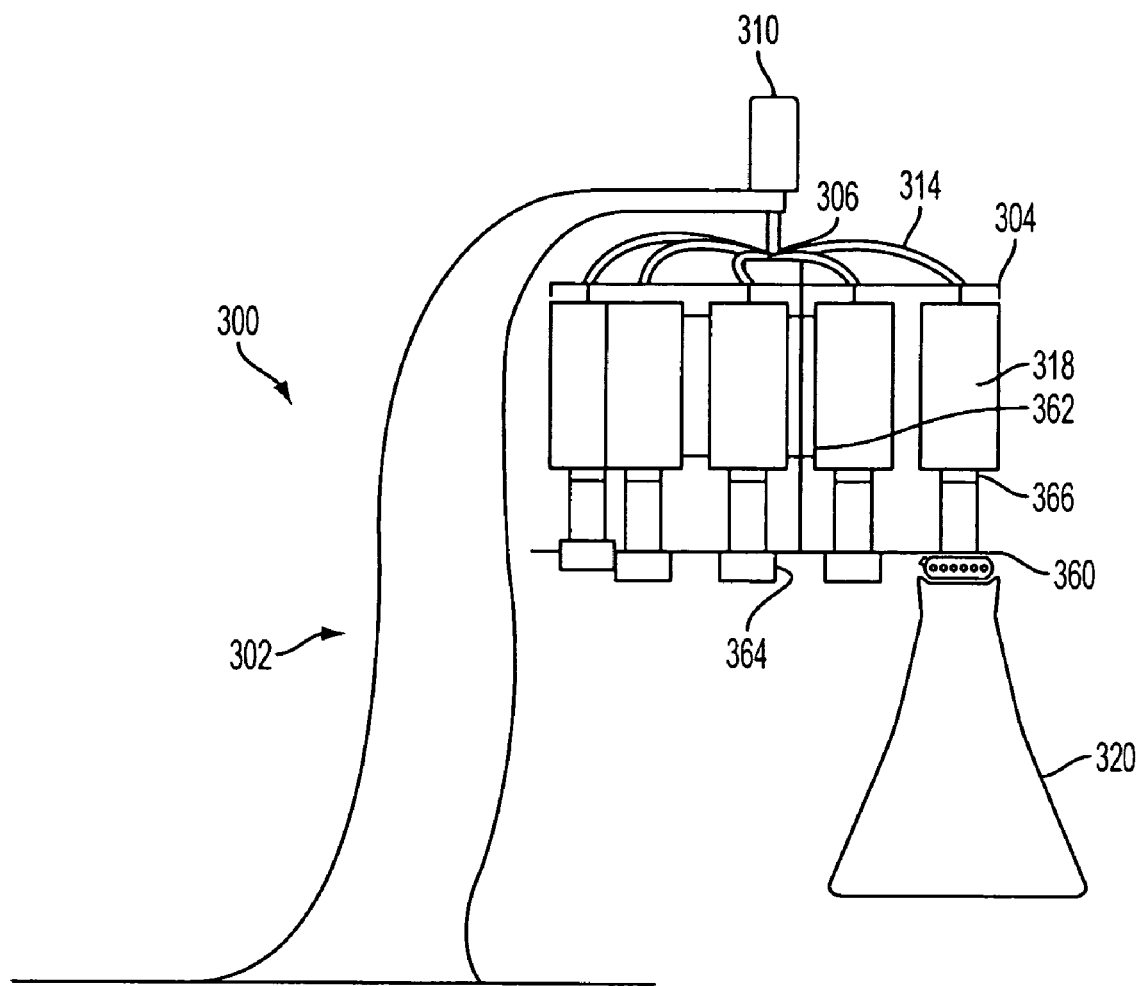
FIG. 13 is a side view illustrating a modification to the carousel arrangement shown in FIG. 8 according to an embodiment of the present invention.
Figure 14:
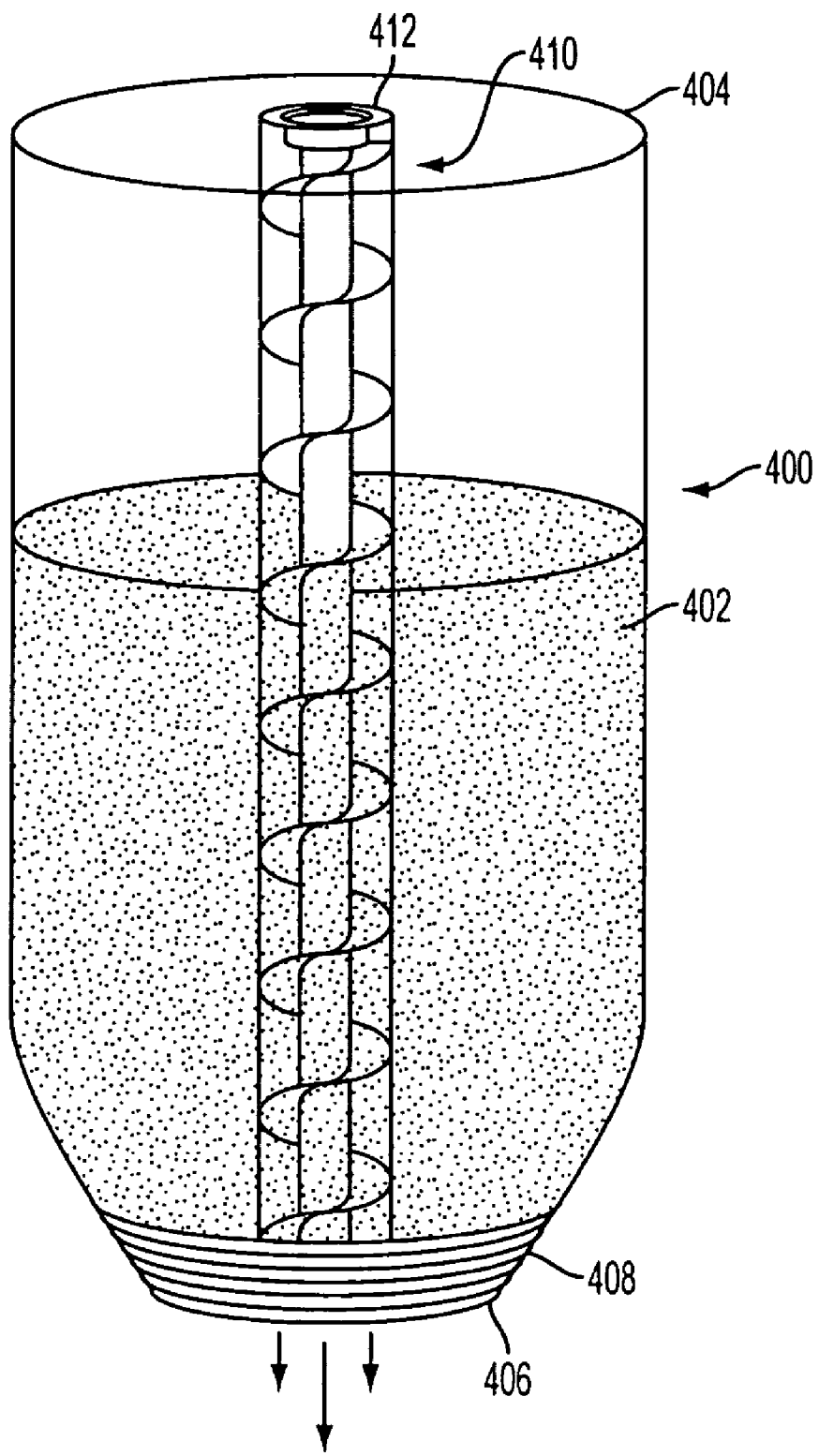
FIG. 14 is a perspective view of a DCM container according to another embodiment of the present invention.
Figure 15:
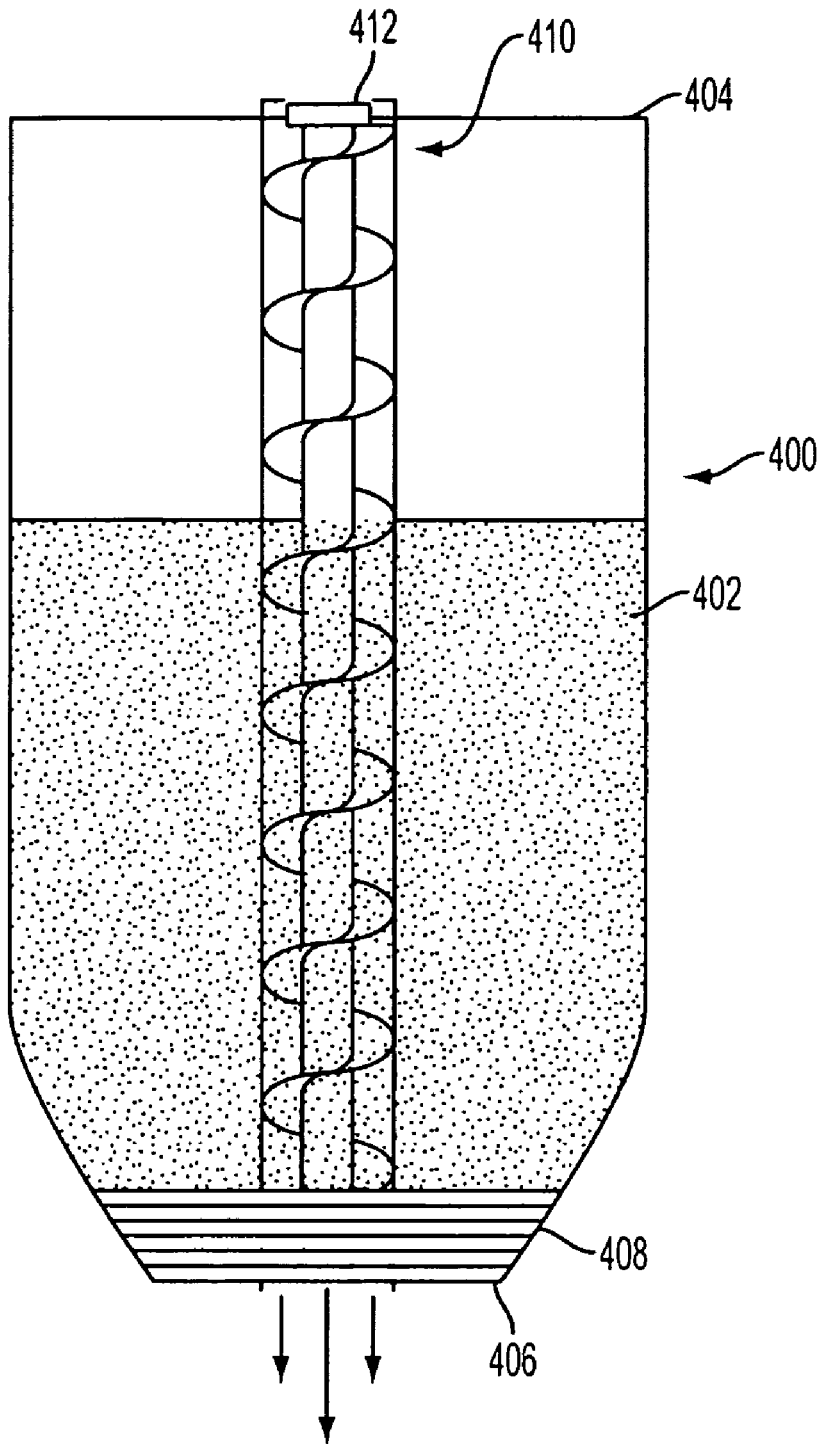
FIG. 15 is a side view of the DCM container shown in FIG. 14.

It should be further noted that the cylinder 328 alternatively may be either an integral part of, or an attachment to, the disposable container 318 or the flask 320. In addition, as shown in FIG. 13, instead of the cylinder 328 coupling to the disposable container 318, the system 300 can include a second rotatable carousel 360 that rotatably couples to the pivot point 308 via a shaft 362, for example, and includes openings 364 that receive different volume cylinders, such as cylinders 328 through 328-3. In this arrangement, a shorter cylinder or adapter 366 having a valve 368 therein that can be opened manually or automatically can be coupled to the bottom opening 326 in the disposable container 318. The different volume cylinders 328 through 328-3 in the rotatable carousel 360 can thus be selectively rotated below the containers 318 so that the desired different volumes of DCM powder can be dispensed into the flask 320 as desired.

In addition, as shown in FIGS. 14-17, an embodiment of the present invention further provides a container 400 that is adaptable for use with any of the configurations or apparatus discussed above. Specifically, the container 400 stores a suitable amount of DCM power 402 in this example, but can be adapted to store any type of material, in particular, granular or powdered material.

The container 400 further includes a top portion 404 and a bottom opening 406. The top portion 404 can be an integral part of the container that is permanently sealed, or can be screwed or snap fit onto the remainder of the container 400 and thus removable from container 400. Alternatively, the top portion 404 can have an opening therein (not shown) that can be covered by, for example, a removable cap or membrane for refilling of DCM powder. The opening 406 can also be covered by a cap or removable or rupturable membrane as discussed above, or by any other suitable device for preventing the undesired leakage of the contents of the container 400.

In addition, for identification purposes, the container 400 can be coded with a color or other indicator representing the contents of the container 400. For instance, this identification can be a color coding (e.g., red, green, blue, etc.) that is present on portions or the entirety of the container 400, a type of indicia (e.g., numbers, letters or alphanumeric symbols) on the container 400 representing the content of the container 400, and/or a bar code representing the content of the container 400. Various safety warnings and other relevant information can also be present on the container 400. Also, the container 400 can be made of any suitable material, such as plastic or various polymers, and can be opaque, or can be translucent so that a technician can readily determine the amount of DCM powder remaining in the container. Furthermore, the mouth of the container 400 is tapered or conical in shape towards the opening 406 so as to allow the DCM powder or other material contained therein to readily flow from the container 400 when the container 400 is set in an upside down position, and includes threads 408 for mating with any of the apparatus discussed above.

As further illustrated, the container 400 includes a device 410 for facilitating movement of the material in the container 400 toward the opening 406. In this example, the device 410 is an auger or auger-like apparatus. The device 410 can be made of any suitable material, such as that of the container, or any other material such as metal, stainless steel and so on. The device 410 includes a bushing 412 that rotatably secures one end of the device 410 to the top portion 404 as shown in more detail in FIG. 16. The other end of the device 410 is rotatably secured to the opening 406 as shown in more detail in FIG. 17, so that the other end of the device 410 is exposed to the opening 406 and thus, the device 410 can facilitate movement of DCM powder or other contents of the container 400 through the opening.

Figure 16:
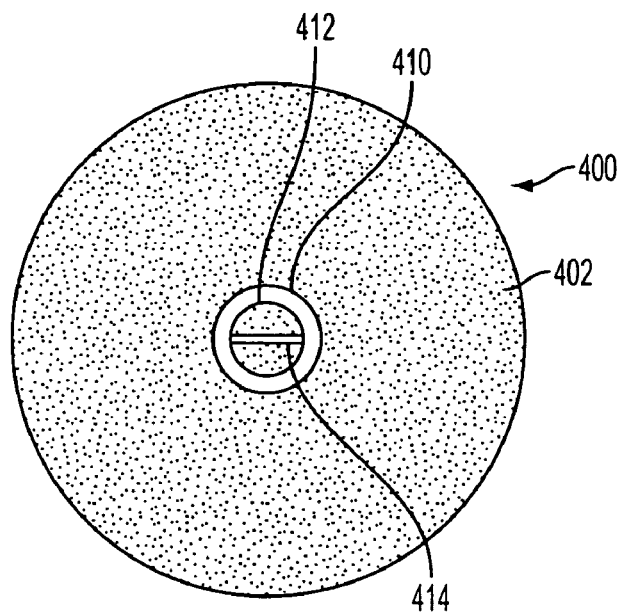
FIG. 16 is a top view of the DCM container shown in FIG. 14.
Figure 17:
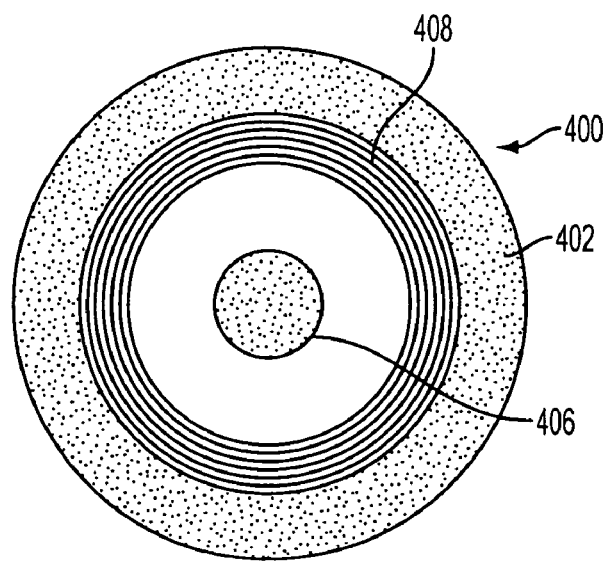
FIG. 17 is a bottom view of the DCM container shown in FIG. 14.
Figure 18:
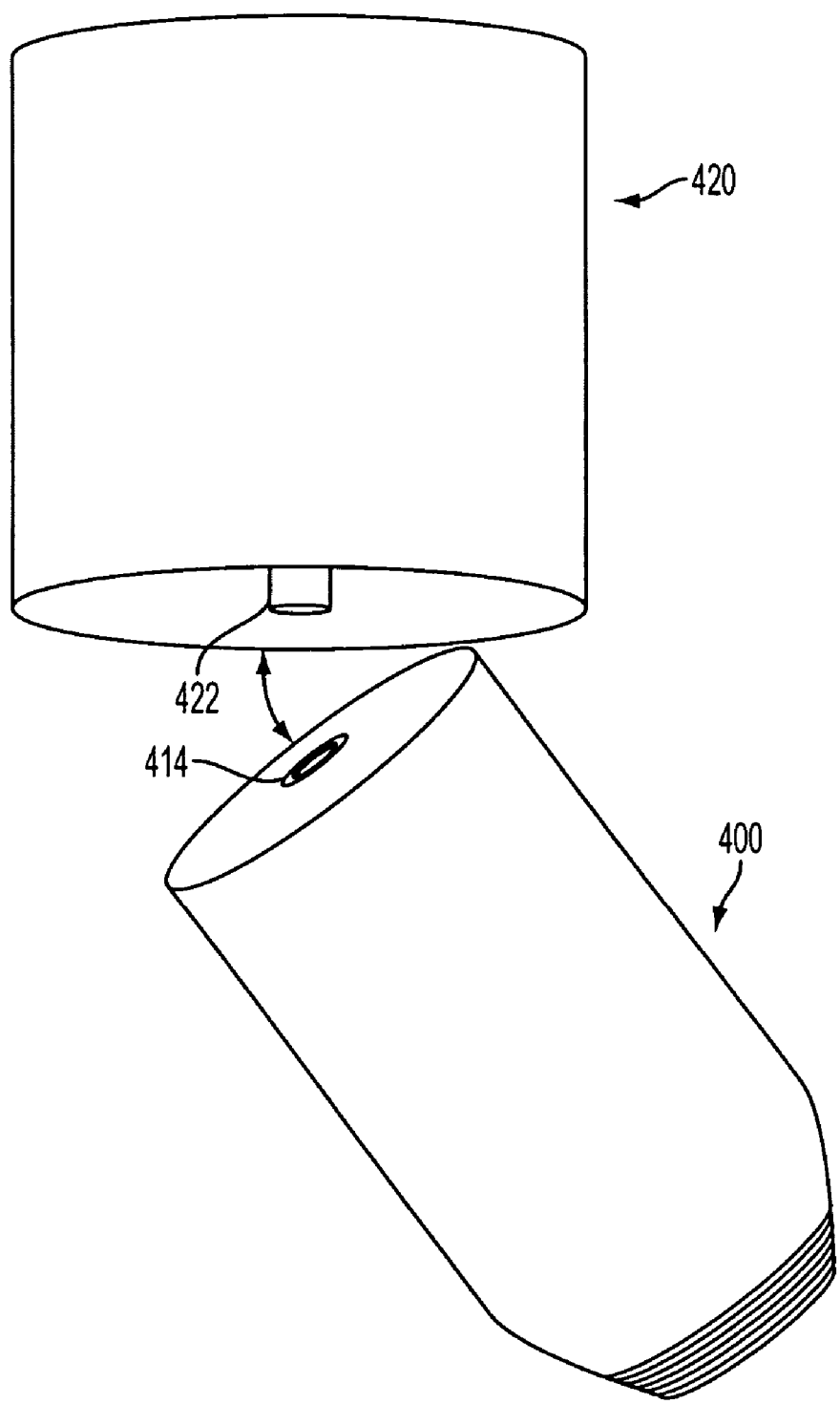
FIG. 18 illustrates an example of the DCM container mating with a motor according to an embodiment of the present invention.

The device 410 is calibrated so that each rotation will result in a predetermined volume of DCM powder (or other contents) being dispensed from the opening 406. As shown in FIGS. 16 and 17, the bushing 412 or end of the device 412 can include a mating portion 414 that can be, for example, a projection or slot for mating with a device, such as a shaft 422 of a motor 420, that can be manually or automatically controlled (e.g., by a computer) to rotate the device 410 at a desired rate of rotation or by a desired number of rotations or partial number of rotations. The container 400 can be attached to the motor 420 by snap-fitting, screwing, clamping or in any other suitable fashion that allows for easy connection to and removal from the motor 420. In another configuration, the motor 420 can be integral with the container 400 or connected to the container 400 as unit. Alternatively, a user can grab the mating portion 414 with his or her fingers, for example, or use any suitable type of manual device, such as a screwdriver, crank or handle, to manually rotate the device 410 at a desired rate or by a desired number of rotations or partial number of rotations.

Accordingly, as will all of the embodiments discussed above, the container 400 allows for dustless or essentially dustless disbursement of DCM power or other material when the container 400 is coupled to any of the apparatus discussed above.

While this invention has been particularly shown and described with reference to preferred embodiments thereof, the preferred embodiments described above are merely illustrative and are not intended to limit the scope of the invention. It will be understood by those skilled in the art that various changes in form and details may be made therein without departing from the spirit and scope of the invention.

What is claimed is:

1. A container system comprising:
   a rotatable device configured to house a plurality of removable containers that are individually removable from the rotatable device, with each of the removable containers including:
   a container portion, configured for storing a powder material therein, the container portion having an integral top portion that is permanently sealed and a bottom portion which is opposite from the top portion and has an opening therein; and
   a movable device, which is disposed inside of the container portion, the movable device having a first end that is coupled to the integral top portion of the container portion and a second end that mates with the opening in the bottom portion of the container portion, the movable device being further configured to prevent the material from exiting the opening in the bottom portion until the movable device is manipulated to facilitate movement of the material from the container portion out of the opening, such that the container portion having the integral top portion and the second end of the movable device configure the container system for dustless disbursement of the powder when the bottom portion of the container portion is coupled to a receiving device which receives the powder that the movable device moves out of the opening in the bottom portion of the container portion.

2. A container system as claimed in claim 1, wherein:
   the movable device comprises an auger, adapted to rotate to facilitate movement of the material out of the opening.

3. A container system as claimed in claim 1, wherein:
   the container portion is adapted to store dehydrated culture media (DCM) powder therein.

4. A container system as claimed in claim 1, wherein:
   at least some of the container portion is tapered toward the opening.

5. A container system as claimed in claim 1, wherein:
   the receiving device comprises a media preparation instrument, wherein:
   the container portion is configured to couple with said receiving device such that said movable device operates to facilitate movement of the material from the container portion out of said opening for delivery into the receiving device while eliminating dust formation of the material outside of the container portion.

6. A container system as claimed in claim 1, wherein: the container portion comprises threads thereon to mate the container portion to the receiving device.

7. A container system as claimed in claim 1, wherein: the movable device comprises a mating portion configured such that when an external force is applied thereto, the external force moves the movable device to facilitate the movement of the material out of said opening in said container portion.

8. A container system as claimed in claim 1, wherein: the rotatable device is configured to couple to a system that operates to position the container portion of one of the removable containers so that the opening of that container portion is in communication with a receiving device that is configured to receive the material.

9. A container system as claimed in claim 1, wherein:
the container portion is adapted to store dehydrated culture media (DCM) powder therein;
the movable device of the container system comprises an auger, adapted to rotate to facilitate movement of the material out of said opening;
the auger comprises first end rotatably secured to a top portion of the container portion, and a second end rotatably secured proximate to the opening, wherein:
the auger comprises a mating portion configured such that when an external force is applied thereto, the external force moves the device to facilitate the movement of the material out of the opening;

the auger is calibrated to dispense a predetermined volume of the material from the opening in the container with each rotation of the auger;

at least some of the container portion is tapered toward the opening; and the container portion is configured to couple with the receiving device, such that the container system operates to facilitate movement of the material from the container portion out of the opening for delivery into the receiving device while eliminating dust formation of the material outside of the container portion.

10. A container system as claimed in claim 1, wherein: the container portion further comprises a sidewall portion that is integral with the integral top portion and the bottom portion; and the first end of the movable device is directly connected to a location on the integral top portion of the container portion that is vertically aligned with the opening in the bottom portion of the container portion, such that the movable device extends along a longitudinal direction of the sidewall portion between the location on the integral top portion and the opening in the bottom portion.

11. A container system as claimed in claim 1, wherein: the first end of the movable device is exposed outside the container portion at the integral top portion of the container portion and the second end of the movable device is exposed at the opening in the bottom portion of the container.

12. A container system as claimed in claim 2, wherein: the auger comprises a first end rotatably secured to a top portion of the container portion, and a second end rotatably secured proximate to the opening.

13. A container system as claimed in claim 2, wherein: the auger is calibrated to dispense a predetermined volume of the powder material from the opening in the container with each rotation of the auger.

14. A container system as claimed in claim 7, wherein: the mating portion is configured to couple with a motor that applies the external force thereto.

15. A container system as claimed in claim 12, further comprising:

a bushing that rotatably secures the auger to the top portion of the container portion.

* * * * *